United States Patent [19]

Lemole

[11] Patent Number: 4,553,554

[45] Date of Patent: Nov. 19, 1985

[54] ELECTRICAL LEAD AND METHOD FOR TEMPORARY CARDIAC PACING

[76] Inventor: Gerald M. Lemole, 404 Tomlinson Rd., Huntingdon Valley, Pa. 19046

[21] Appl. No.: 530,532

[22] Filed: Sep. 9, 1983

[51] Int. Cl.[4] .............................................. A61N 1/04
[52] U.S. Cl. .................................. 128/784; 128/419 P
[58] Field of Search ............ 128/642, 419 P, 784–786

[56] References Cited

U.S. PATENT DOCUMENTS

| 2,985,172 | 5/1961 | Jones | 128/784 |
|---|---|---|---|
| 3,367,339 | 2/1968 | Sessions | 128/419 P |
| 3,437,091 | 4/1969 | Jerushalmi et al. | 128/419 P |
| 3,543,761 | 12/1970 | Bradley | 128/784 |
| 3,664,347 | 5/1972 | Harmjanz | 128/419 P |
| 3,949,757 | 4/1976 | Sabel | 128/786 |
| 4,030,509 | 6/1977 | Heilman et al. | 128/784 |
| 4,033,333 | 7/1977 | DeSalvo et al. | 128/639 |
| 4,141,365 | 2/1979 | Fischell et al. | 128/419 R |
| 4,144,889 | 3/1979 | Tyers et al. | 128/785 |
| 4,291,707 | 9/1981 | Heilman et al. | 128/784 |
| 4,313,448 | 2/1982 | Stokes | 128/785 |
| 4,374,527 | 2/1983 | Iverson | 128/785 |
| 4,407,302 | 10/1983 | Hirshorn et al. | 128/419 P |
| 4,444,195 | 4/1984 | Gold | 128/786 |

Primary Examiner—Kyle L. Howell
Assistant Examiner—Ruth S. Smith
Attorney, Agent, or Firm—Robert J. Mooney

[57] ABSTRACT

An improved electrical lead and the associated surgical procedure for using the same to connect the heart of a post-operative patient temporarily to an external cardiac pacemaker. An elongated non-conductive carrier housing a pair of insulated signal wires is provided with a pair of contact plates at separate locations along the surface of the carrier. Each of the plates is connected to one of the signal wires. The contact plates are configured and spaced apart to provide intimate electrical contact with the external walls of the atrium and ventricle when the carrier is placed in proper position dorsal to the heart.

7 Claims, 7 Drawing Figures

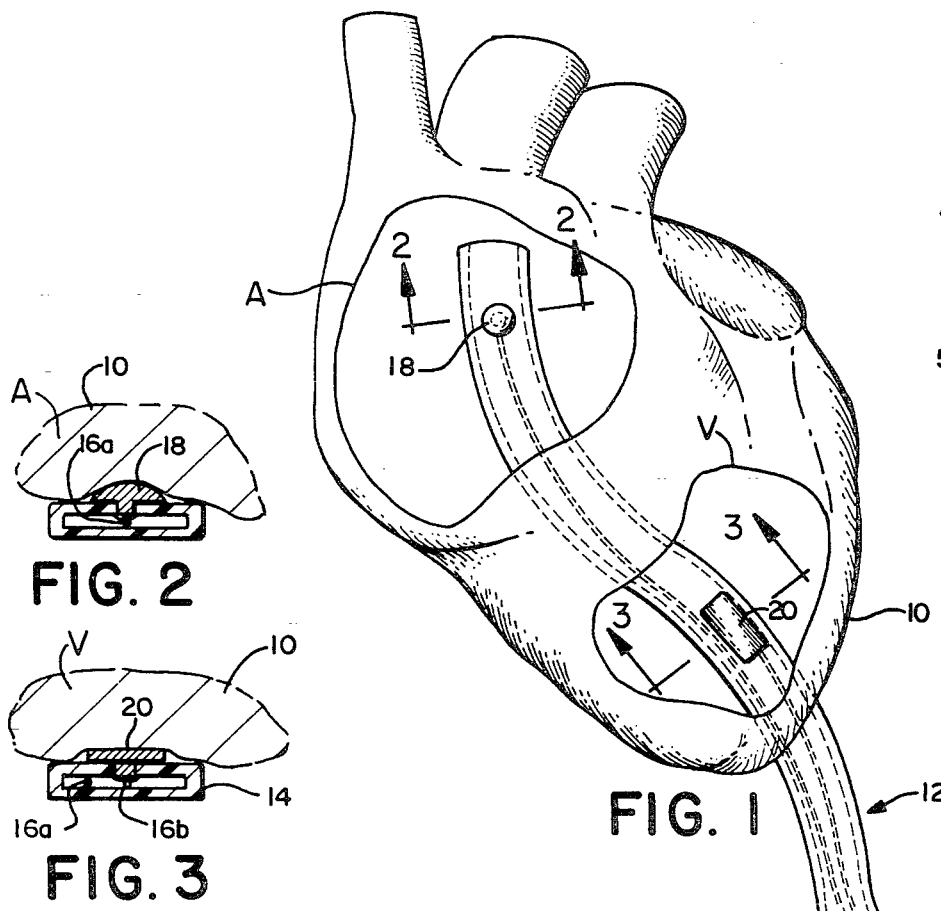
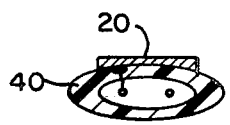
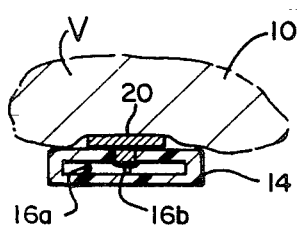
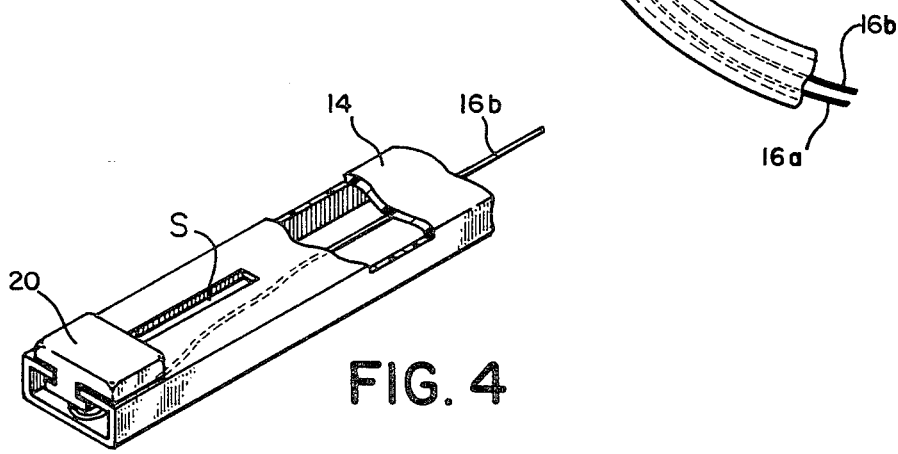

ELECTRICAL LEAD AND METHOD FOR TEMPORARY CARDIAC PACING

BACKGROUND OF THE INVENTION

The present invention relates to surgical devices and procedures, and more particularly to an improved electrical lead and associated method of using the same for temporarily connecting a heart to an external pacemaker.

In the postoperative period following heart surgery, it sometimes becomes necessary to temporarily assist the heart of a patient using an external cardiac pacemaker. In such situations, insulated lead wires are typically sutured to the heart wall prior to chest closure to provide proper electrical contacts for effective pacemaker operation. After the chest of the patient is closed, the wires, which extend from the heart through the skin, can be easily connected to the pacemaker for applying appropriate electrical stimulation to the heart. When the pacemaker is no longer needed, the protruding lead wires are pulled from the sutures thereby breaking them free from the heart wall so that the surgeon may withdraw the wires completely out of the body through the skin.

The practice of first suturing lead wires to the heart wall and then pulling them from the wall to accomodate the temporary use of an external cardiac pacemaker can have undesirable consequences. Firstly, suturing the lead wires into electrical contact with the heart can cause a severe trauma to the heart, which obviously is to be avoided with a heart patient. Secondly, pulling the sutured lead wires from the heart wall can result in serious tissue damage to the heart wall.

SUMMARY OF THE INVENTION

Accordingly, it is a general purpose and object of the present invention to provide an improved electrical lead and associated method of using the same for temporarily connecting a heart to an external cardiac pacemaker.

It is a more particular object of the present invention to provide a sutureless electrical lead for external cardiac pacing of a patient during postoperative periods that is easily yet effectively placed in electrical contact with the heart while permitting safe and complete removal when cardiac pacing is no longer necessary.

It is a further object of the present invention to provide an electrical lead for temporary cardiac pacing that makes intimate and secure physical and electrical contact with the appropriate heart walls without being sewn or otherwise anchored thereto.

It is a still further object of the present invention to provide an electrical lead for connecting the heart to an external pacemaker that is simple yet reliable in performance, relatively inexpensive to manufacture, and easily adapted to existing surgical procedures.

Briefly, these and other objects of the present invention are accomplished as follows. An elongated non-conductive carrier, housing a pair of insulated signal wires, is provided with two contact plates which are secured to the surface of the carrier at separate locations. Each contact plate is connected to one of the two signal wires. The contact plates are configured and spaced apart to provide intimate electrical contact with the walls of the atrium and ventricle when the carrier is placed in the preferred position dorsal to the heart.

In use, the carrier is placed beneath the heart during surgery and caused to protrude at one end thereof through the skin of the patient so that the wires may be connected to the pacemaker. Maintained in proper position by the weight of the heart and surrounding body structures, the carrier, along with the wires housed therein, are slidingly removed from beneath the heart and withdrawn from the body after the need for the external pacemaker has ended.

For a better understanding of these and other aspects of the present invention, reference may be made to the following detailed description taken in conjunction with the accompanying drawing in which like reference numerals designate like parts throughout the figures thereof.

BRIEF DESCRIPTION OF THE DRAWING

FIG. 1 is a frontal view of a heart, partially cut away for clarity, showing employment of an electrical lead beneath the heart in accordance with the present invention;

FIG. 2 is a sectional view of the atrial portion of the electrical lead shown in FIG. 1 taken along the line 2—2;

FIG. 3 is a sectional view of the ventricle portion of the electrical lead shown in FIG. 1 taken along the line 3—3;

FIG. 4 is a perspective view of an alternate ventricle portion of the electrical lead of the present invention; and FIGS. 5(a), 5(b) and 5(c) are sectional views of alternate configurations of the electrical lead according to the present invention.

DESCRIPTION OF THE PREFERRED EMBODIMENT

Referring now to FIG. 1, an electrical lead, generally designated 12, is shown properly disposed for use in applying temporary electrical stimulation to a heart 10 from an externally located cardiac pacemaker (not shown). Placed in position beneath heart 10 during surgery, lead 12 comprises an elongated non-conductive carrier 14 fabricated from a biocompatible elastic material, such as silicone rubber, that is substantially non-reactive upon exposure to body fluids. Other suitable materials for carrier 14 include various plastics, specifically Delrin and Teflon, both trademarks of E. I. Dupont DeNemours and Company. Carrier 14 is preferrably formed having a substantially rectangular configuration, better viewed in FIGS. 2 and 3, and is hollow along its length, the carrier being flexible for ease of manipulation and placement yet sufficiently rigid to maintain its proper position in situ. The rectangular configuration is preferred because the flat surfaces virtually eliminate rotation of the carrier 14 with respect to the heart after the carrier 14 is emplaced. The carrier 14 may be of any suitable length with typical transverse profile dimensions of six to seven millimeters in width and two to three millimeters in thickness. It should be noted that the carrier 14 should exhibit sufficient longitudinal tensile strength so as to avoid fracturing at any point when pulled upon at its external end at time of removal from the body, as discussed in greater detail hereinafter.

Contained within and routed longitudinally through carrier 14 are a pair of insulated signal wires 16a and 16b for conducting the appropriate pacemaker signal through carrier 14. The signal wires 16a and 16b are constructed of a malleable, conductive metal substantially non-reactive upon exposure to body fluids, such as a platinum-iridium alloy. Having their one ends adapted for connection to the external pacemaker (not shown), the respective signal wires 16a and 16b are electrically connected at their opposite ends to an atrial contact 18 and a ventricular contact 20 mounted at separate locations along the outer surface of carrier 14.

Referring now to FIG. 2 in conjunction with FIG. 1, the atrial contact 18 is firmly mounted near the internal end of carrier 14 opposite the end connected to the external pacemaker (not shown). Connected to signal wire 16a within carrier 14, the atrial contact 18 serves to apply appropriate electrical stimulation to the atrium A of heart 10 by firmly abutting the heart wall beneath the atrium. Atrial contact 18 is made from a biocompatible, chemically non-reactive metal, such as stainless steel, and is formed in the shape of a hemisphere to provide an increased current density between the contact and the wall of the atrium A of heart 10. Typically, having a diameter of about two millimeters, atrial contact 18 may include a pair of hemispheric elements both electrically connected to signal wire 16a and spaced slightly apart from each other to ensure effective contact with the wall of atrium A.

Referring now to FIG. 3 in conjunction with FIG. 1, the ventricular contact 20 mounted upon carrier 14 is located along the length thereof at a certain distance, typically about ten centimeters, from the atrial contact 18 depending upon the size of heart 10. Connected to signal wire 16b, the ventricular contact 20 is situated along carrier 14 to intimately press upon the wall of heart 10 beneath the ventricle V thereof and thereby apply appropriate electrical stimulation to the ventricle from the external pacemaker (not shown). The venticular contact 20, fabricated from the same metallic material used for atrial contact 18, is formed as a rectangular plate, typically having a thickness of about one millimeter and rectangular dimensions of about ten millimeters long by five millimeters wide, corresponding to the respective longitudinal and transverse axes of carrier 14.

Referring now to FIG. 4, an alternate mounting of ventricular contact 20 permits sliding longitudinal adjustment of the location of the contact over a limited distance usually forty to fifty millimeters, to accomodate a range of heart sizes. A longitudinal slot S, the length of which determines the adjustment range, is formed along the top surface of carrier 14 in the vicinity of the average fixed location of the ventricular contact 20. Adapted to slidingly engage the slot S and be frictionally retained therein, the ventricular contact 20 may be moved over the length of the slot S to provide the proper location for applying ventricular stimulation.

In FIGS. 5(a), 5(b), and 5(c) alternate configurations of the carrier 14 shown in FIG. 1 and suitable for use in the present invention are viewed in cross-sections through the ventricle contact 20. In FIG. 5(a), carrier 30 is a solid rectangular body wherein signal wires 16a and 16b are imbedded for routing to the respective contacts 18 and 20. A hollow, flattened cylindrical carrier 40, substantially similar to a surgical chest tube, is illustrated in FIG. 5(b) and is a suitable alternative for housing the signal wires 16a and 16b and mounting the contacts 18 and 20. A solid, flattened cylindrical carrier 50 shown in FIG. 5(c) with imbedded signal wires 16a and 16b may also be used in accordance with the present invention.

It should be understood that a ground contact (not shown) may be provided on the underside of the particular carrier employed and a third signal wire then used to ground the external pacemaker (not shown) to the patient. However, a more simple alternative for grounding would be to suture any equipment ground directly to the skin of the patient.

A surgical procedure for using the electrical lead 12 to apply temporary electrical stimulation to heart 10, as required, is described as follows. After virtual completion of surgery on the patient and following the determination of the patient's need for temporary use of an external pacemaker during post-operative recovery, the electrical lead 12, fabricated and assembled as described above, is placed beneath the heart 10 so that the atrial contact 18 and ventricular contact 20 are respectively positioned directly under the external walls the atrium A and the ventricle V of the heart 10. The heart 10 is caused to rest upon carrier 14 thereby producing intimate and secure connections between the atrial contact 18 and the external wall of the atrium A as well as the ventricular contact 20 and the external wall of the ventricle V, which connections effectively transmit the appropriate electrical stimulations to heart 10 from the external pacemaker (not shown). Carrier 14 and the respective contacts 18 and 20 are maintained in proper position by the weight of heart 10 and surrounding body structures (not shown). Following the need for pacemaker stimulation, the entire electrical lead 12 (which includes carrier 14, signal wires 16a 16b, and contacts 18 and 20) may be slidingly removed from beneath the heart 10 and withdrawn from the body of the patient through his skin by pulling upon the external end of carrier 14 after disconnection of the external pacemaker (not shown).

Therefore, it is apparent that the disclosed invention provides an improved electrical lead and associated surgical procedure for using the same to temporarily connect the heart of a post-operative patient to an external cardiac pacemaker. More particularly, the disclosed invention provides a sutureless electrical lead for temporary cardiac pacing that is easily and effectively connected to a heart requiring such stimulation, while permitting safe and complete removal from the body when the cardiac pacing is no longer deemed necessary. The disclosed electrical lead makes intimate and secure contact with the appropriate external walls of the heart without being sewn or otherwise anchored thereto. Furthermore, the disclosed electrical lead is simple yet reliable in performance, relatively inexpensive to manufacture, and easily adapted to existing surgical procedures.

Obviously, other embodiments and modifications of the present invention will readily come to those of ordinary skill in the art having the benefit of the teachings presented in the foregoing description and drawings. It is therefore to be understood that various changes in the details, materials steps, and arrangement of parts, which have been described and illustrated to explain the nature of the invention, may be made by those skilled in the art within the principle and scope of the invention as expressed in the appended claims.

I claim:

1. A lead for applying electrical stimulation to a heart from an external pacemaker, comprising:
 a pair of wire means each adapted for communicating electrical stimulation from a pacemaker to the heart;
 an elongated non-conductive means housing said wire means, said non-conductive means being formed having a slot along a portion of the length thereof;

a first electrical contact means connected to one of said wire means and fixed upon said non-conductive means so as to be adapted for intimate contact with the wall of the atrium of the heart; and a second electrical contact means connected to the other of said wire means and movably mounted upon said non-conductive means within said slot at an adjustable longitudinal distance apart from said first contact means so as to be adapted for intimate contact with the wall of the ventricle of the heart.

2. An electrical heart lead according to claim 1, wherein:

said first contact means is formed in the shape of a hemisphere; and said second contact means is formed in the shape of a rectangular means plate.

3. An electrical heart lead according to claim 2, wherein:

said non-conductive means is formed having a substantially rectangular cross-sectional configuration.

4. An electrical heart lead according to claim 3, wherein:

said non-conductive means is hollow along its length.

5. An electrical heart lead according to claim 2, wherein:

said non-conductive means is formed having a substantially flattened, cylindrical cross-sectional configuration.

6. An electrical heart lead according to claim 5, wherein:

non-conductive means is hollow along its length.

7. A surgical method for providing temporary electrical stimulation to a heart using an electrical lead of the type wherein a pair of signal wires are carried within an elongated non-conductive member and separately connected to respective ones of a pair of electrical contacts mounted along the member, comprising the steps of:

placing the lead in a position dorsal to the heart so that the electrical contacts are maintained by the weight of the heart directly adjacent the respective walls of the atrium and ventricle;

routing the lead from beneath the heart and out through the skin so that the elongated member and signal wires protrude therefrom;

connecting the protruding signal wires of the lead to a cardiac pacemaker for required electrical stimulation of the heart; and withdrawing the lead from beneath the heart and out through the skin following the required stimulation.

* * * * *